US008182434B2

(12) United States Patent
Thaler et al.

(10) Patent No.: US 8,182,434 B2
(45) Date of Patent: May 22, 2012

(54) EQUINE LOCOMOTOR FLEXION ALGOMETRY DEVICE (ELFA)

(76) Inventors: Roland Alois Thaler, Metamora, MI (US); Walter Uebelacker, Herrsching (DE)

( * ) Notice: Subject to any disclaimer, the term of this patent is extended or adjusted under 35 U.S.C. 154(b) by 1000 days.

(21) Appl. No.: 12/127,899

(22) Filed: May 28, 2008

(65) Prior Publication Data

US 2009/0299227 A1 Dec. 3, 2009

(51) Int. Cl.
*A61B 5/103* (2006.01)
(52) U.S. Cl. .......... 600/587
(58) Field of Classification Search .......... 600/587, 600/446
See application file for complete search history.

(56) References Cited

U.S. PATENT DOCUMENTS 3,670,574 A 6/1972 Edwards
5,092,052 A * 3/1992 Godsey .......... 33/265
5,722,555 A * 3/1998 Polzl .......... 220/812
6,033,370 A 3/2000 Reinbold
6,038,935 A 3/2000 Fullen
6,224,548 B1 5/2001 Gopinathan et al.
6,320,510 B2 * 11/2001 Menkedick et al. .......... 340/573.1
6,500,119 B1 * 12/2002 West et al. .......... 600/437
6,979,164 B2 12/2005 Kramer
7,012,593 B2 3/2006 Yoon et al.
2003/0006998 A1 * 1/2003 Kumar .......... 345/700
2004/0019382 A1 * 1/2004 Amirouche et al. .......... 623/18.11
2006/0058667 A1 * 3/2006 Lemmerhirt et al. .......... 600/446
2007/0289379 A1 * 12/2007 You et al. .......... 73/379.03

FOREIGN PATENT DOCUMENTS

JP 06189980 7/1994
JP 9285581 11/1997
JP 10185941 7/1998
JP 2001070288 3/2001
WO 2006002313 1/2006

* cited by examiner

*Primary Examiner* — Max Hidenburg
*Assistant Examiner* — Mehari Kidanemariam
(74) *Attorney, Agent, or Firm* — David L King

(57) ABSTRACT

A cordless handheld equine leg flexibility testing device 100 has a handheld assembly module 10, a power source 12, a data storage module 20, and either a leg holder assembly 60 or a hoof holder assembly 40 which is removably attached to the handheld assembly module 10 and are interchangeable depending on the test being performed.

15 Claims, 15 Drawing Sheets

100
42
48
44
40
43
41
45
94
11
10

EQUINE LOCOMOTOR FLEXION ALGOMETRY DEVICE (ELFA)

TECHNICAL FIELD

This invention relates to a hand held device used to apply a constant pressure on a horse's limb to provide a more uniform way to evaluate a horse for lameness.

BACKGROUND OF THE INVENTION

The value of a horse is often determined by the soundness of the animal's physical structure which requires the person evaluating an animal to make certain observations such as checking the animal's teeth, eyes, coat, hooves and overall general shape. These visual cues give some indication as to the animal's condition; however, they provide little indication of the horse's ability to perform or its locomotor ability. Often horses can have a condition or weakness that can result in lameness. As early as 1850 a flexion test was being used as a clinical tool to diagnose a horse's limbs for lameness.

This flexion test requires a clinician to apply a force on a limb held in a flexed position for one minute, in some cases the test is conducted over a one and a half minute period. The horse is then trotted off to observe lameness.

Many in the field of equine evaluations such as horse trainers and veterinarians have determined this method of evaluating a horse for lameness is very subjective. The ability of the person conducting a flexion test varies depending on the strength of the person, the ability to apply a uniform force on the flexed limb and on experience. Typically an experienced adult male conducting the flexion test applies an average force of 150 Newtons with a variation of slightly greater than 10% during a test. And even more significantly, the average applied force can vary greatly, for example during a single test the average force instead of being 150 Newtons can vary between 100 and 175 Newtons. Females generally apply a mean force of 110 Newtons in a report published in 1997 by P. R. Keg et al entitled "Variations in the force applied to flexion tests of the distal limb of horses" published in Veterinary Record (1997) 141, 435-438.

This study acknowledges the variations in the test were so great that one could not rely on the test as a tool for evaluating a horse for lameness. The same horse may pass the test if the force applied was well below the average 150 Newtons, but the animal would show lameness if the higher force of 150 was maintained over the full minute duration.

As a result, the study showed the flexion test was critically flawed. The study used a prototype device to measure or quantity the force applied referred to as a flexometer.

The flexometer device was a cumbersome piece of equipment. A force transducer was designed which consisted of a rounded polyvinylchloride plate, with about the same curvature as the hoof of an adult horse, to which an air-filled rubber tube was fixed. The air pressure within the tube is measured by an electronic manometer at the outlet of the tube, the signal from which was pre-amplified in a charge amplifier. The output signal was visualized on a numerical display, and can be fed to a chart recorder. The device was calibrated by applying a known force to the device while simultaneously recording the output and measuring the actual force (in Newtons) by means of a steelyard.

A line extended approximately 8 to 10 feet from the curved plate with the rubber tube lining the plate to the meter which in turn was connected by another line to a chart. The person conducting the test needed to observe the force readings on the meter while holding the horse and not getting entangled in the lines. This device worked adequately in a controlled test environment as several persons were actively involved, one holding the horse, one monitoring the chart and the test performance and one actually conducting the test. The problems of using such a device on a non-experimental basis are numerous.

The person conducting the test may or may not have one or more assistants, the horse may or may not stand still and avoid getting entangled in the numerous lines, the access to a/c power outlets may not exist at the location where the animal is to be tested and the ability to read a digital display can be affected by the distance the operator is located from it and the amount of sun glare if the test is conducted outside. These are just a few examples of the problems associated with this prototype device.

The present invention had as an objective to provide a greatly improved device that was capable of making the flexion tests not only much more uniform and therefore reliable, out actually made conducting this important test easy to perform.

A further objective was to make a device suitable for a wide range of horse hoof sizes.

Another objective was to improve the design to make it a portable self contained device free of all line connections during the actual test and made so all force measurements were stored in the device itself so the operator's attention and focus was always on the animal being evaluated.

These and other objectives are achieved by the present invention described as follows.

SUMMARY OF THE INVENTION

A cordless handheld equine leg flexibility testing device has a handheld assembly module, a power source, a data storage module, and either a leg holder assembly or a hoof holder assembly which are removably attached to the handheld assembly module and are interchangeable depending on the test being performed.

The handheld assembly module has a housing which holds a load sensor cell attached to the housing. A base plate covers the housing and is attached to the load cell sensor and spaced from the housing such that the base plate can move under load transferring the load to the load cell which measures any applied forces being transmitted through the base plate to the load cell. The leg holder assembly is removably attached to the base plate of the handheld assembly. The power source for activating the load cell preferably includes rechargeable batteries or other similar devices for powering the load cell and the data storage module. The data storage module is internal of the housing and provides a way of receiving data from the load cell to collect force measurements exhibited by deflection of the load cell during testing and provides for transmitting the received date to an external separate computer or a chart recording device after testing. The data storage device is capable of storing numerous tests and transferring the individual test data to the external computer or chart recording device when so desired.

Both the leg holder assembly and the hoof holder assembly are designed to be removably attached to the base plate of the handheld assembly module. The hoof holder assembly is interchangeable with the leg holder assembly and is used to provide a way of stabilizing and holding the hoof of the limb being tested. The leg holder assembly is designed to hold the leg portion of the animal being tested and to transmit forces directly to the load cell.

The cordless handheld leg flexibility testing device further has an electronic circuit board connected to the load surface sensor for measuring the start and duration of a test, and the force being applied. An audio signal device is connected to the electronic circuit board to provide an audible tone indicating the completion of a test and any overloading or underloading forces. These conditions such as the completion of the test or an overload or underload force is communicated by emitting an audible sound alarm, preferably each of these conditions has its own distinct audible sound, whether it be a louder tone or a series of beeps indicating whether an overload condition or underload condition is occurring or whether the test is in fact completed.

Both the hoof holder assembly and the leg holder assembly have a conformable surface for contacting and supporting the test animal's leg or hoof. This conformable surface provides a way of insuring that the maximum amount of surface area of the animal's leg or hoof is in contact with the holder assembly and that these holder assemblies can transmit the load directly to the base plate which then transmits the load deflection to the load cell which is then measured as a force being applied to the animal. Preferably the conformable surface is an elastomeric material. The elastomeric material may be a compressible polyurethane foam with an outer skin. These materials are often called "memory foam".

The leg holder assembly is preferably arcuately curved transverse to the length of the leg holder assembly to form a substantially parallel supporting channel surface for the limb of the test animal relative to the handheld assembly module. The shape of the leg holder channel is a somewhat truncated "U" shaped such that it can cradle the limb of the animal in a very comfortable position.

The hoof holder assembly has an inclined "L" shaped surface relative to the handheld assembly module. The hoof holder extends from an upper end to a lower end along a substantially planar surface. At the lower end a short, bent portion extends upwardly from the inclined planar surface to form an "L" shape for supporting and immobilizing the hoof of the test animal during the test procedure.

Both the leg holder assembly and the hoof holder assembly each have mounting structures below the support surfaces. The mounting structures are for slidable attachment to the base plate of the handheld assembly module. The base plate of the handheld assembly module has protruding guide surfaces for accepting the mounting structures, and the mounting structures have complimentary guide channels for sliding onto the protruding guide surfaces of the base plate. Upon assembly these guide surfaces provide a means of positioning and securing both the hoof holder assembly and the leg holder assembly. The base plate and the mating mounting structures further have a detent locking pin to fix the holder assemblies for removable attachment.

In a preferred embodiment the handheld device further includes a wifi transmitter assembly connected to the electronic circuit board for wireless transmission of data, also the handheld assembly module may further have a removable electronic flash card connected to the electronic circuit board for data storage retrieval. The handheld assembly module may further have a USB port connected to the circuit board to permit stored data to be downloaded to a computer after testing. Any one or all three of these means for transferring stored data may be employed with the hand held device. In an alternative embodiment, the handheld device may also be provided with a remote load indicator device for attachment to the wrist of the tester. The remote indicator device has a visual load display activated by a wireless transmission from the handheld assembly module. This wireless transmission communicates with the wrist worn indicator device and may provide a visual display that will include a numeric display or a color code indicating an underload or overload condition or a proper loading condition, in such a case the indicator light will be red for an underload or overload condition and green for a proper load condition if so desired. This wrist held device further will store the data transmitted and can be used to communicate with a laptop computer later if so desired for data transmission as a fourth alternative of transmitting the information from the device to a storage laptop or other computer storage device.

In another alternative embodiment, the base plate may be provided with a centrally located attachment hemispherical shaped locator post. Each leg holder assembly and hoof holder assembly which are removably attached can be located on the hemispherical shaped locator post wherein each holder assembly can be pivotably moved slightly relative to the handheld assembly module. In such a case, the devices will snap onto this hemispherical shaped locator post in such a way that they can pivot about the hemispherical shaped locator post such that loads can be substantially normally to the load cell regardless to the orientation of the leg or hoof during the test procedure.

BRIEF DESCRIPTION OF THE DRAWINGS

FIG. 8 is a schematic illustration of a test using the hoof holder assembly on the front distal limb of a horse.

FIG. 9 is a schematic view showing the leg holder assembly being used to evaluate the front upper limb of a test animal.

FIG. 10 illustrates the device with the hoof holder assembly wherein the hind distal limb is being tested.

FIG. 11 illustrates the hoof holder assembly attached to the testing device for evaluating the hind upper limb.

FIG. 12 shows the leg holder assembly being applied to the hind upper limb of a test animal.

DETAILED DESCRIPTION OF THE INVENTION

Figure 1:
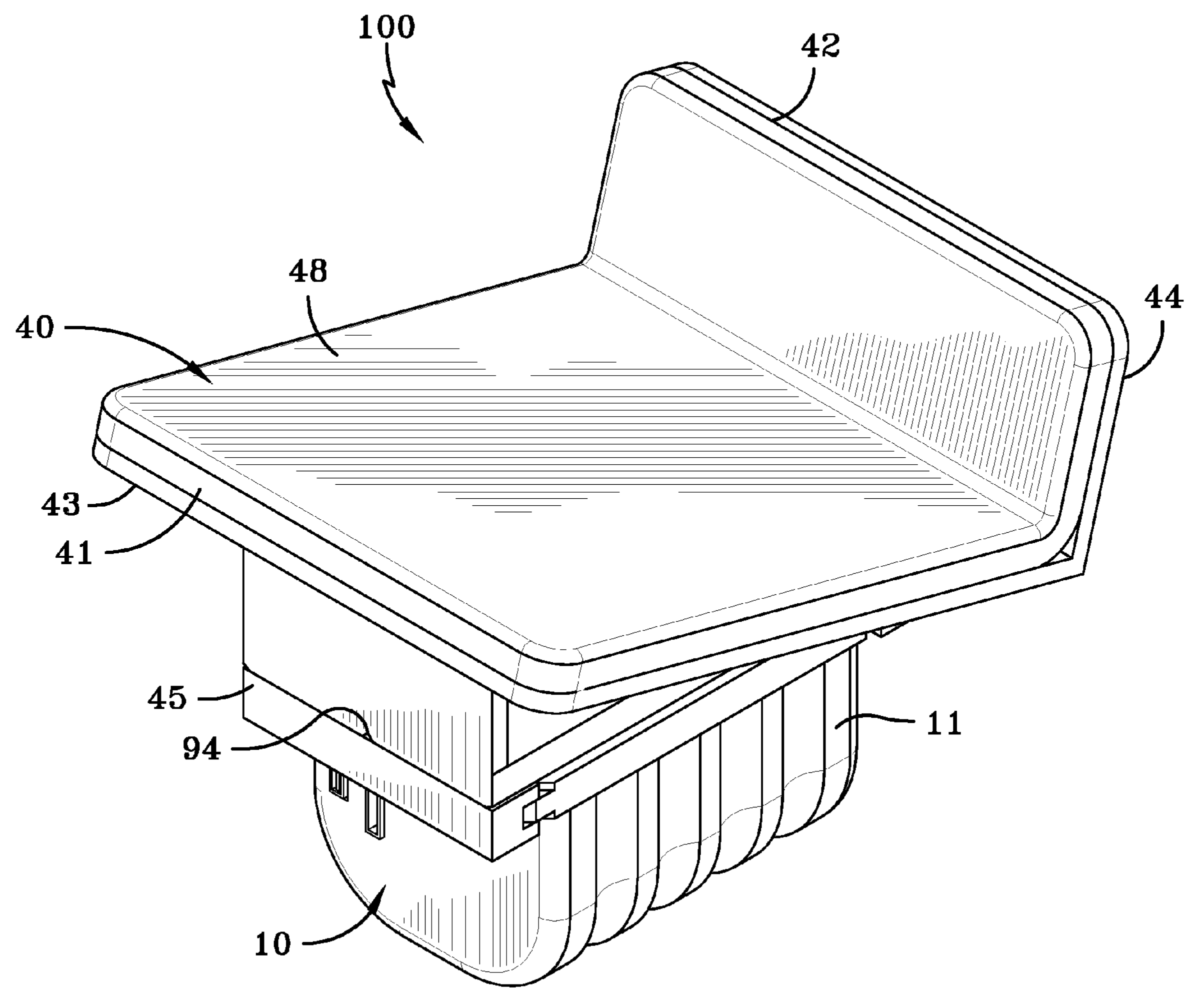
FIG. 1 is a perspective view of the cordless handheld equine leg flexibility testing device made according to the present invention.
Figure 5:
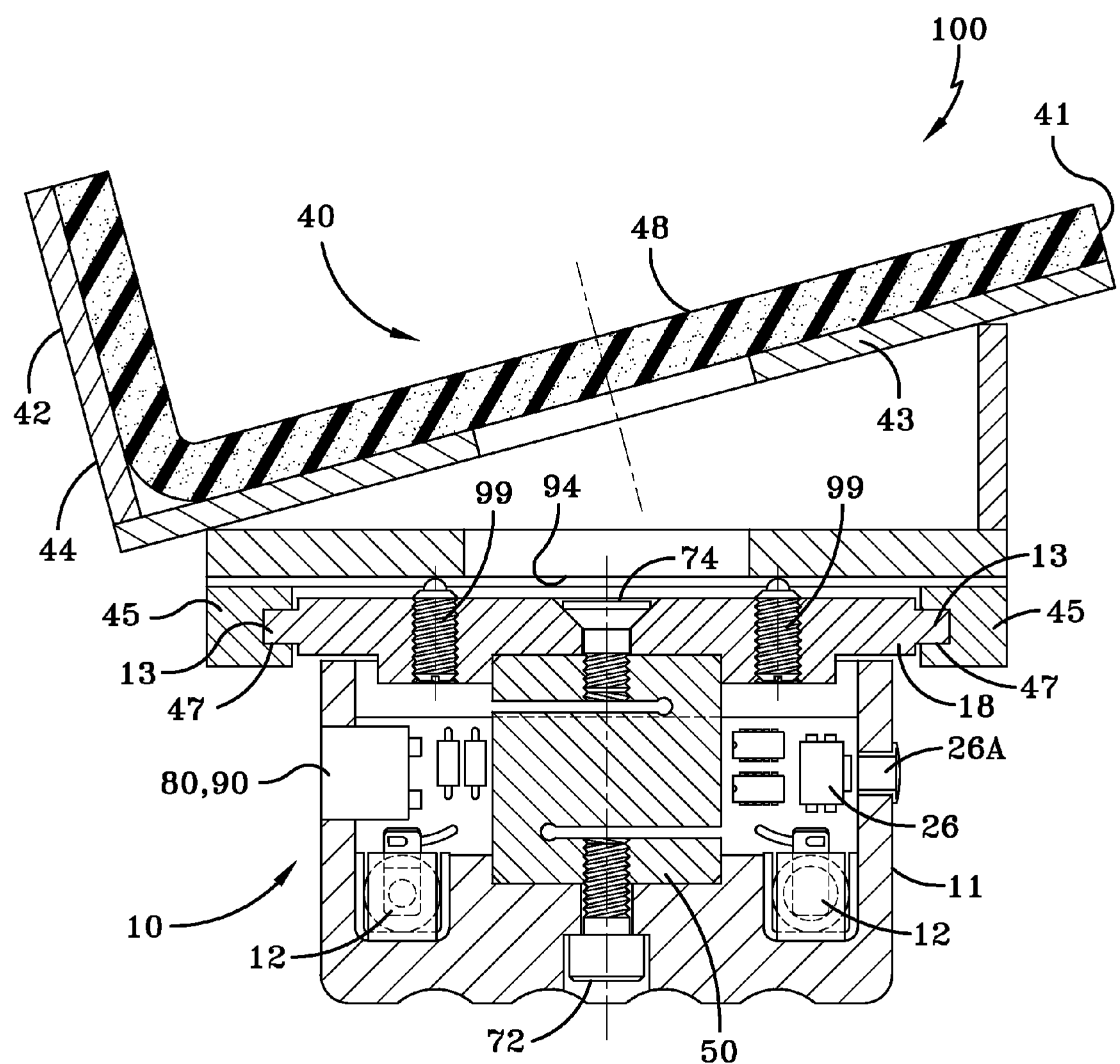
FIG. 5 is a cross sectional view of the hoof holder assembly mounted on the handheld assembly module.

With reference to FIGS. 1 and 5, the cordless handheld equine leg flexibility testing device 100 made according to the present invention is shown. The device 100 has a handheld assembly module 10 containing a power source 12, a data storage module 20 and other associated components for collecting and storing data. Attached to the handheld assembly module 10 is a hoof holder assembly 40 which is removably attached to the housing structure 11 of the module 10. The hoof holder assembly 40 is designed specifically to position and locate a horse's hoof such that the leg and hoof region can be properly oriented during a leg flexibility test.

Figure 2:
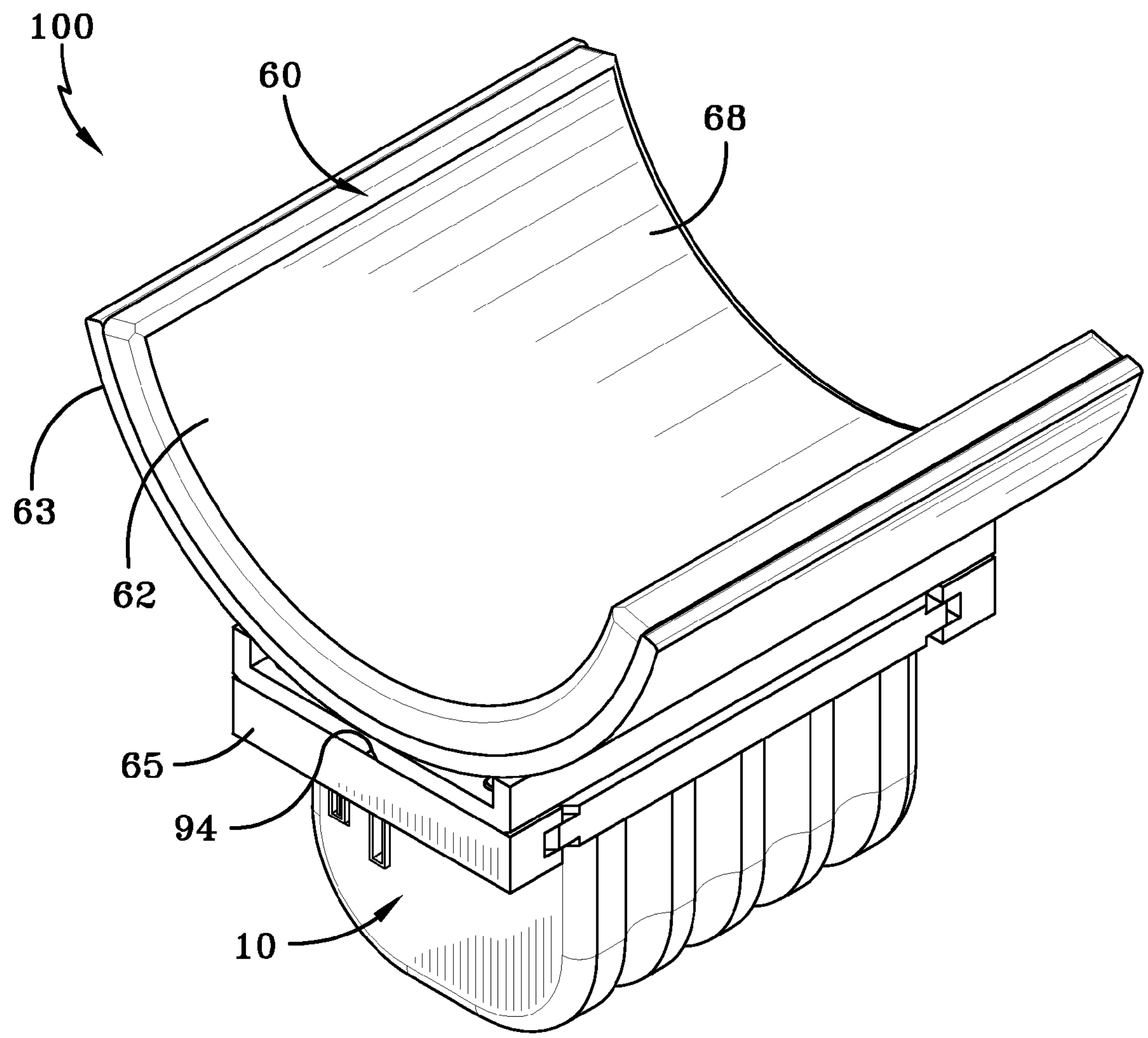
FIG. 2 is a perspective view of the cordless handheld equine leg flexibility testing device with the interchangeable leg holder assembly attached to the handheld assembly module.

With reference to FIG. 2, a perspective view of the cordless handheld equine leg flexibility testing device 100 is shown with an interchangeable leg holder assembly 60 attached to the handheld assembly module. The leg holder assembly 60 has a generally "U" shaped structure that is adapted to support a leg during the testing of the animal.

Figure 3:
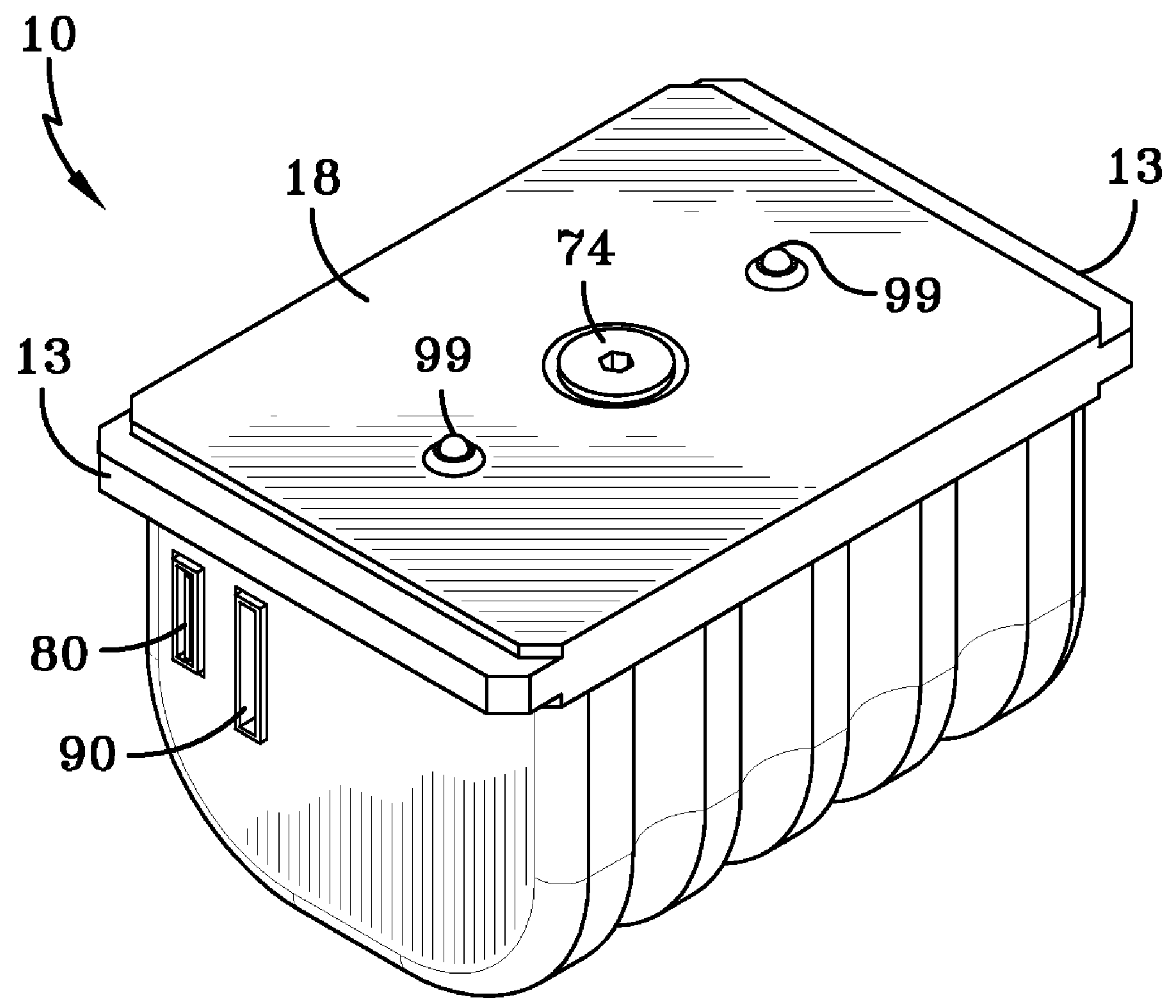
FIG. 3 is a perspective view of the handheld assembly module with the leg holder or hoof holder removed.
Figure 3A:
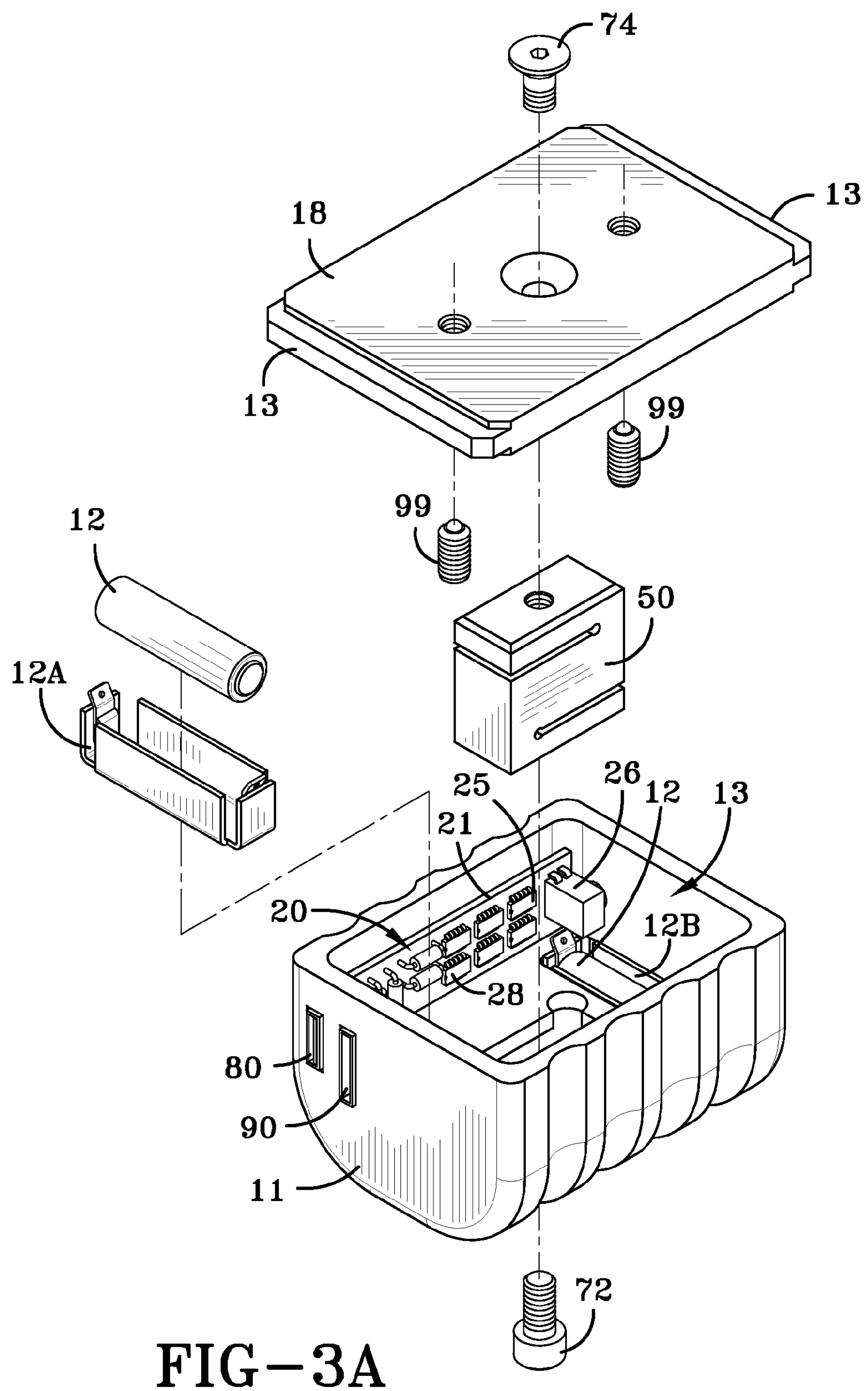
FIG. 3A is an exploded view of the handheld assembly module.
Figure 4:
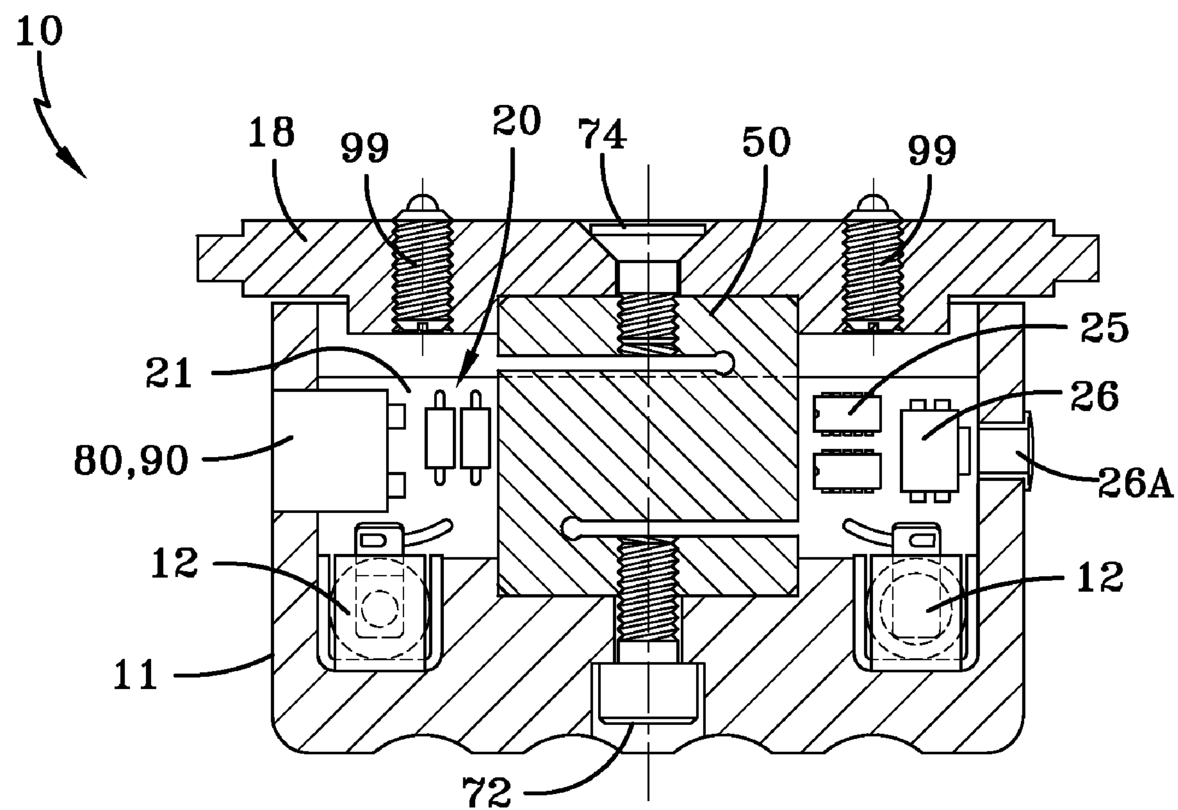
FIG. 4 is a cross sectional view of the handheld assembly module.

With reference to FIGS. 3, 3A and 4, the handheld assembly module 10 is shown with the leg holder assembly 60 or hoof holder assembly 40 removed. FIG. 3 shows the housing structure 11 with a base plate cover 18 while FIG. 3A is an exploded view to expose the internal workings of the handheld assembly module 10. The handheld assembly module 10 holds a load sensor cell 50 which is physically attached by a fastener 72 in the bottom of the housing. The base plate cover 18 as shown in FIG. 3A in an exploded view is attached by a fastener 74 to the load sensor cell 50 directly and is spaced from the housing structure 11 so that the base plate cover 18 can move under load transferring the load to the load cell 50 which measures any applied forces being transferred through the base plate cover 18 to the load cell 50.

In the internal cavity 13 of the housing structure 11, a power source 12 is positioned which may include rechargeable batteries 12 snapped into battery holders 12A and 12B or other similar devices for powering the load cell 50 and powering a data storage module 20. The data storage module 20 is internal of the housing structure 11 and provides a way of receiving data from the load cell 50 to collect force measurements exhibited by deflection of the load cell 50 during testing and provides for transmitting the received data to an external separate computer or a chart recording device after the testing is completed. The data storage module 20 includes an electronic circuit board 21 which is capable of storing numerous tests and transferring individual test data to the external computer or chart recording device when so desired.

As shown in FIGS. 3 and 3A in a preferred embodiment, the handheld device module 10 can include a wifi transmitter chip 25 connected to the electronic circuit board 21 for wireless transmission of data. Also the handheld assembly module 10 may further have an electronic flash card port 90 connected to the electronic circuit board 21 for data storage retrieval. The handheld assembly module 10 may further have a USB port 80 connected to the circuit board 21 to permit stored data to be downloaded to a computer after testing as shown in FIG. 4. Any one or all three of these means for transferring stored data may be employed with the hand held device 100.

The cordless handheld leg flexibility testing device 100 has the electronic circuit board 21 wired or otherwise connected to the load cell sensor 50 and measures the length and duration of the test as well as capturing the force being applied to the load cell 50. Preferably an audio signal device 26 is connected to the electronic circuit board 21 to provide an audible tone indicating the completion of a test and any overloading or underloading forces. These conditions such as the completion of the test or an overload or underload force is communicated by emitting an audible sound alarm through the screened opening 26A, preferably each of these conditions has its own distinct audible sound, whether it be a louder tone or a series of beeps indicating whether an overload condition, an underload condition is occurring or whether the test is in fact completed.

With reference to FIG. 4 a cross sectional view of the handheld assembly module 10 is shown wherein the base plate 18 is connected to the load cell 50 as indicated wherein the transfer of forces can be conducted by movement of tire base plate 18 inwardly causing a deflection on the load cell 50 which then transmits to a force being applied to the load cell 50 to the data storage module 20.

One of the distinct features of the present device is that it is cordless and provides no wires or other encumbrances in which the horse or the testers can become entangled during the test procedure. This unit is completely self sufficient and provides a way of gathering load force data and time measurements in a simple and easy manner. One of the key advantages of the present design is that the device 100 is provided with an interchangeable leg holder assembly 60 and hoof holder assembly 40 uniquely designed to provide support for the animal's leg or hoof during the test procedure. The ability to load the animal's hoof is uniquely different than supporting the leg and applying force. As such it is desirable that two unique holders be provided for each of these locations on the test animal.

As shown in FIG. 5, the hoof holder assembly 40 has an inclined "V" shaped surface relative to the handheld assembly module 10. The hoof holder extends from an upper end 41 to a lower end 42 in a substantially planar support structure 43. At the lower end 42 a short, bent or upright portion 44 extends upwardly from the inclined planar support structure 43 to form an "L" shape for supporting and immobilizing the hoof of the test animal during the test procedure.

Figure 6:
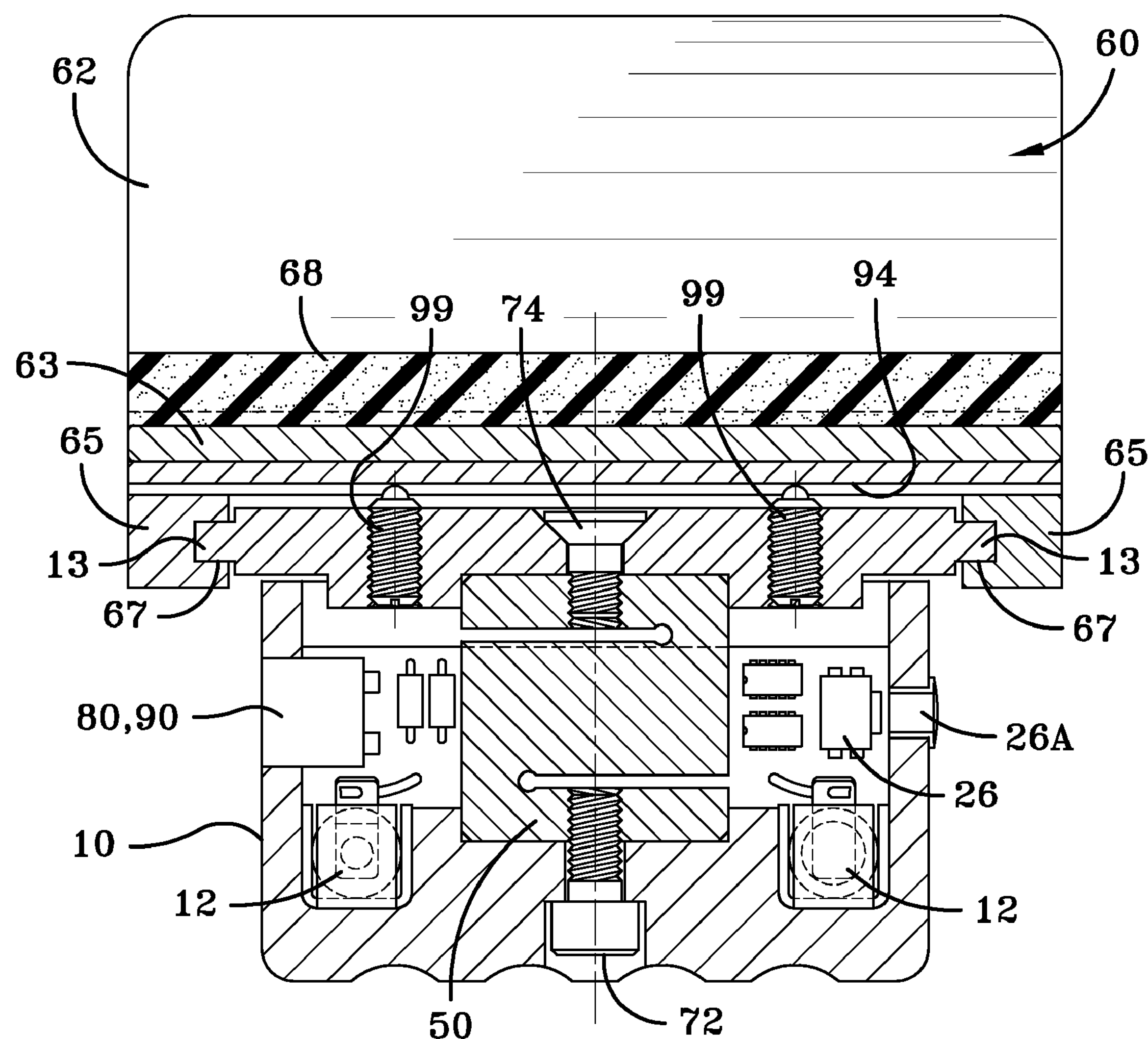
FIG. 6 is a cross sectional view of the leg holder assembly mounted on the handheld assembly module.

With reference to FIG. 6, a cross sectional view of the leg holder assembly 60 is illustrated. The leg holder assembly 60 is preferably arcuately curved transverse to the length of the leg holder assembly 60 to form a substantially parallel supporting channel 62 for the limb of the test animal relative to the handheld assembly module 10. The shape of the leg holder support structure 63 is a somewhat truncated "U" shape such that it can cradle the limb of the animal in a very comfortable position.

Both the hoof holder assembly 40 and the leg holder assembly 60 have a conformable surface 48, 68 for contacting and supporting the test animal's leg or hoof. This conformable surface 48, 68 provides a way of insuring that the maximum amount of surface area of the animal's leg or hoof is in contact with the holder assembly 40, 60 and that these holder assemblies 40, 60 can transmit the load directly to the base plate cover 18 which then transmits the load deflection to the load cell 50 which is then measured as a force being applied to the animal. Preferably the conformable surfaces 48, 68 are made of an elastomeric material. The elastomeric material may be a compressible polyurethane foam with an outer skin. These materials are often called "memory foam".

Both the leg holder assembly 60 and the hoof holder assembly 40 each have mounting structures 45, 65 below the support surfaces 43, 63. The mounting structures 45, 65 are for slidable attachment to the base plate cover 18 of the handheld assembly module 10. The base plate cover 18 of the handheld assembly module 10 has protruding guide rails 13 for accepting the mounting structures 45, 65. The mounting structures 45, 65 have complimentary guide channels 47, 67 for sliding onto the protruding guide rails 13 of the base plate cover 18. Upon assembly these guide rails 13 provide a means of positioning and securing either the hoof holder assembly 40 or the leg holder assembly 60 to the module. The base plate cover 18 and the mating mounting structures 45, 65 may further have detent locking pins 99 that snap into a channel or groove 94 to fix the holder assemblies 40, 60 for removable attachment.

Figure 7:
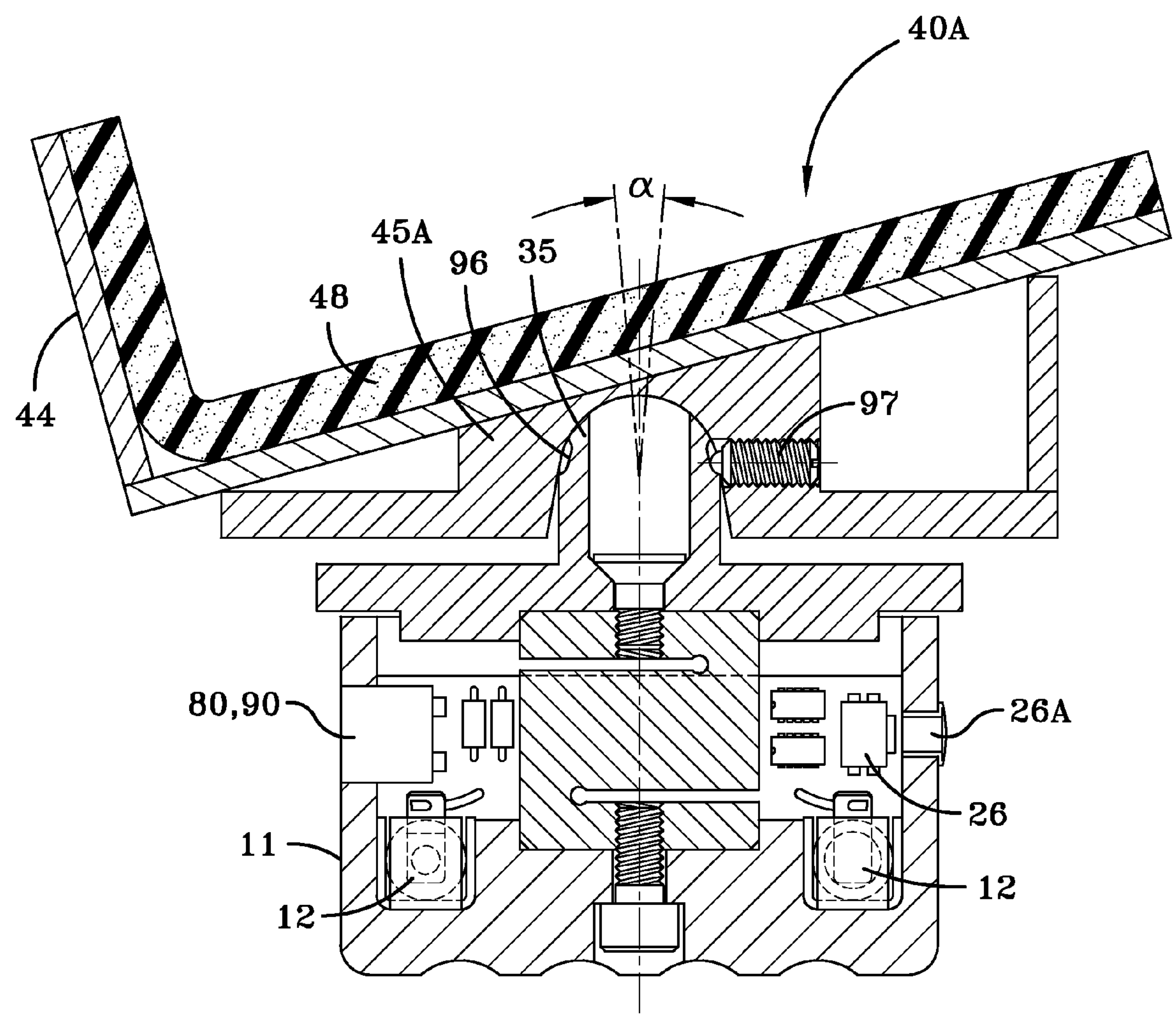
FIG. 7 is a cross sectional view of an alternative embodiment of the present invention showing a snap on device for supporting and locating the hoof holder assembly or the leg holder assembly onto the base plate of the handheld assembly module.

As shown in FIG. 7, an alternative embodiment may be employed wherein the base plate cover 18 may be provided with a centrally located snap on post attachment hemispherical shaped locator post 35. Each leg holder assembly and hoof holder assembly can be removably attached can be located on the hemispherical post shaped locator post 35 wherein each holder assembly 40A or 60A (60A not shown, but having the features of 60 with the mounting of this alternative embodiment) can be pivotably moved slightly relative to the handheld assembly module 10. In such a case, the holder devices will snap onto this locator post 35 in such a way that they can pivot slightly about the locator post 35 such that loads can be substantially normalized relative to the load cell 50 regardless to the orientation of the leg or hoof during the test procedure. As shown a detent pin 97 fits into a groove 45A to hold the holder assembly 40A onto the locator post 35. Gaps created between the mounting structure of the holder 40A and the cover 18 allows the holder 40A to pivot about an angle alpha. This greatly insures that the loads are transmitted at an angle generally perpendicular to the load cell 50, this is important in that it provides a more accurate reading of the amount of force being applied to either the leg or the hoof.

As shown the device 100 is extremely portable and made extremely durable to withstand the rigors of equine testing. The test device 100 permits the tester to test numerous horses by coding in the number of the horse and test procedure and at a later time this data can be transmitted to a computer for data storage as previously discussed.

With reference to FIGS. 8-12, the cordless handheld leg flexibility testing device 100 according to the present invention is shown in various exemplary test positions to evaluate flexion tests conducted on the limbs 4, 6 of a horse 2.

Figure 8:
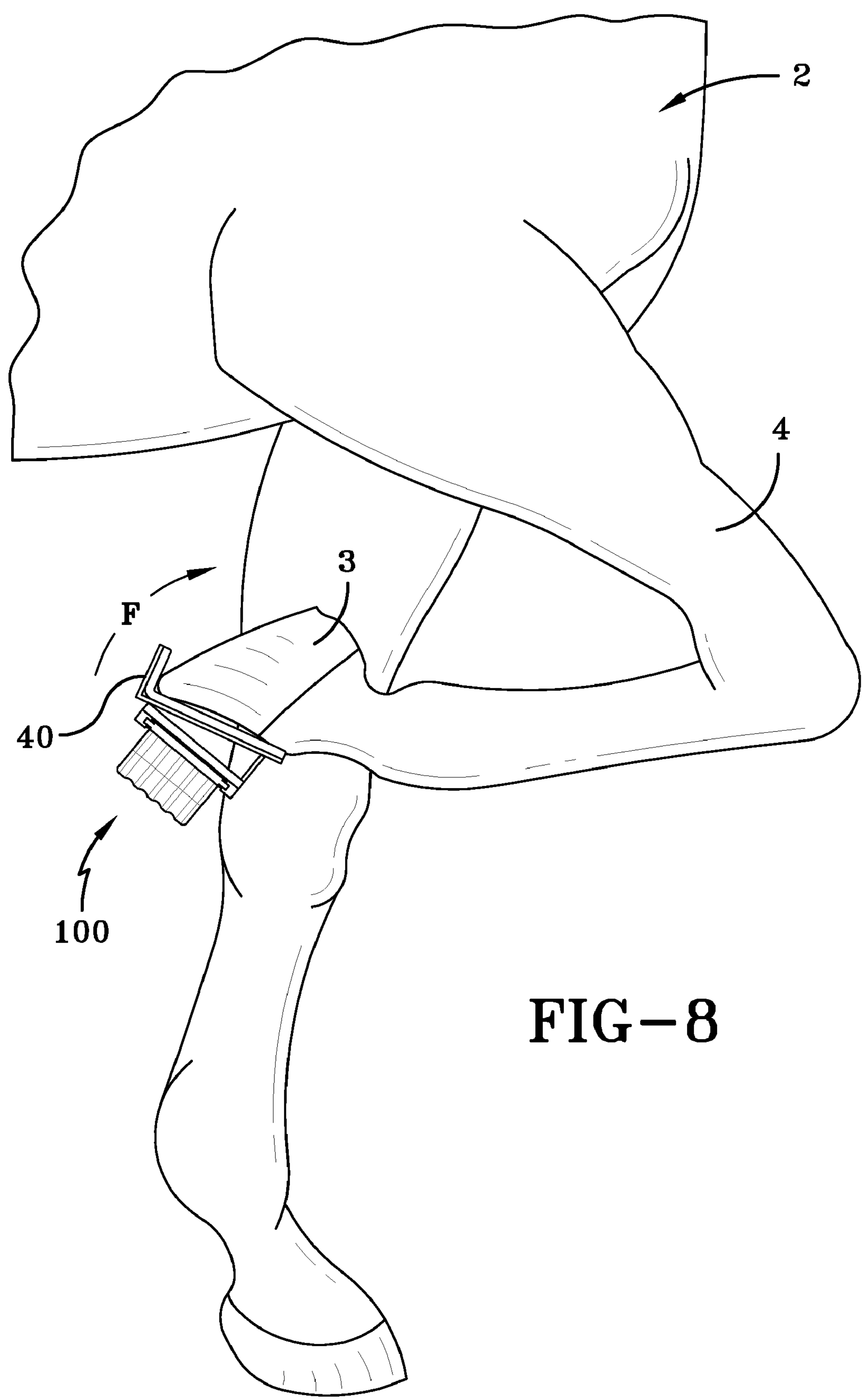
FIGS. 8-12 illustrate the cordless handheld leg flexibility testing device being used in various tests on a test animal.

With reference to FIG. 8, a schematic illustration of the test device 100 is shown being used with a hoof holder assembly 40 on the front distal limb of a horse. As shown when a tester applies a force F onto the hoof 3 of the horse 2 using the inclined "L" shaped bracket hoof holder assembly 40. The hoof 3 is bent in the direction of the leg 4 as shown. This test will be conducted for approximately 30 to 90 seconds, one minute is the typical test procedure.

Figure 9:
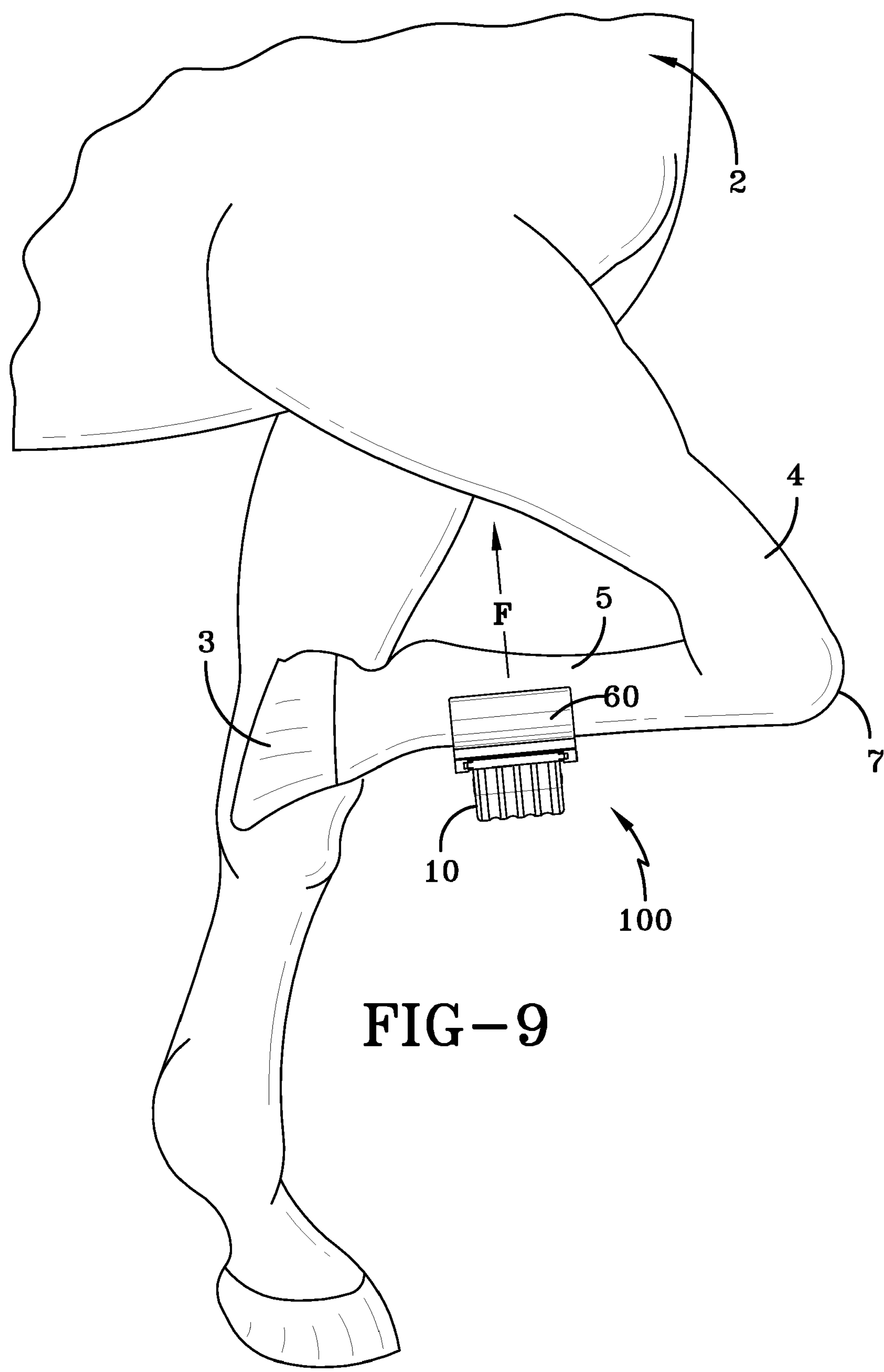

With reference to FIG. 9, a leg holder assembly 60 is shown attached to the assembly module 10 wherein the leg portion 5 just below the knee 7 and above the hoof 3 is cradled in the leg holder 60 assembly and an upward force is applied on the animal's leg 4 bending it towards the animal's body while the leg 4 is bent at the knee 7 as shown.

Figure 10:
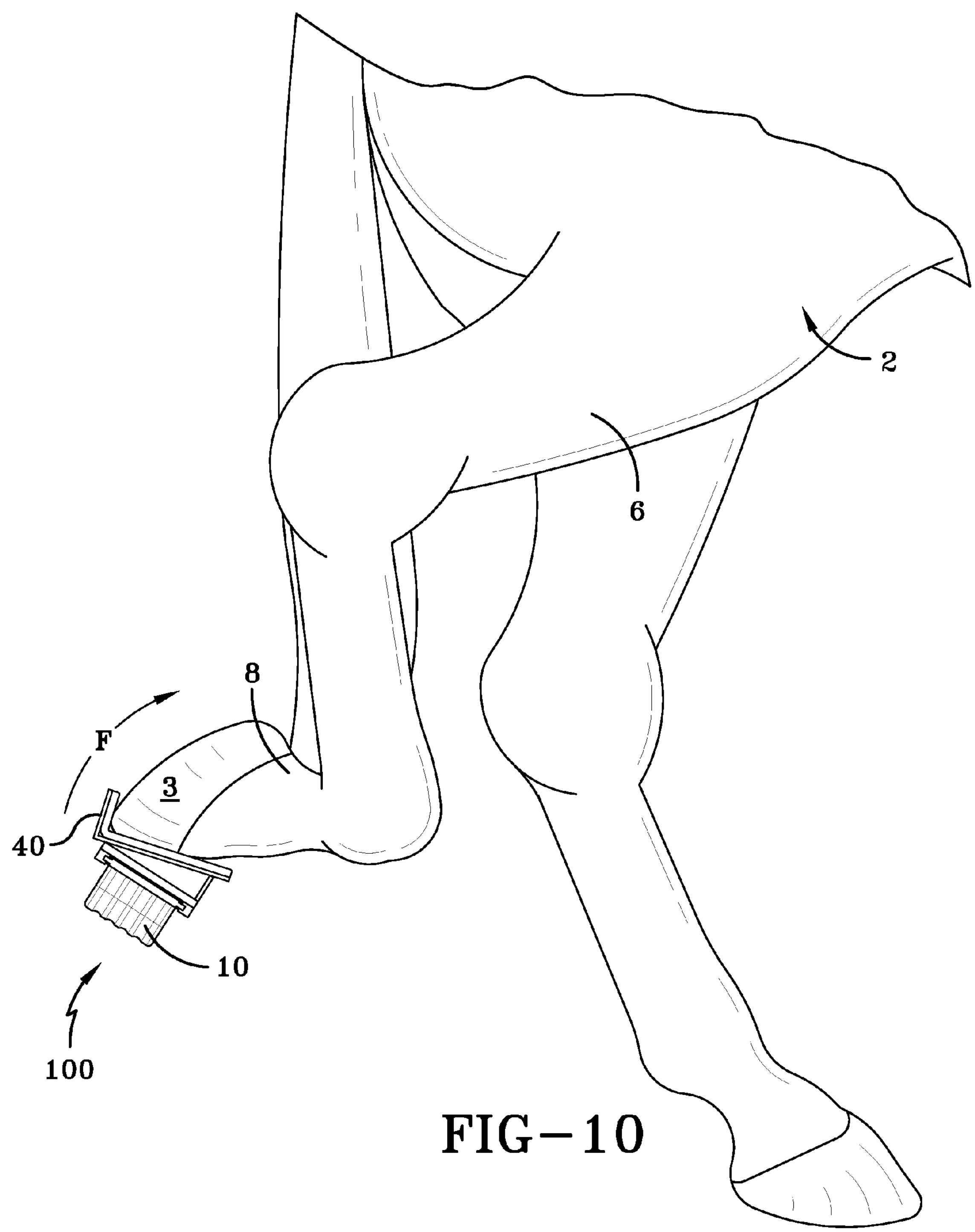

With reference to FIG. 10, device as illustrated with the hoof holder assembly 40 wherein the hand distal limb 6 is being tested. In this case a tester (not shown) stands beside the horse 2 raising the rear leg 6 upwardly while providing a bending action on the hoof 3. The hoof 3 is cradled in the hoof holder assembly 40 such that it is physically restrained by the bent upward portion 44 of the holder 40. As shown a force is then applied back toward the body of the horse in a bending action as illustrated.

Figure 11:
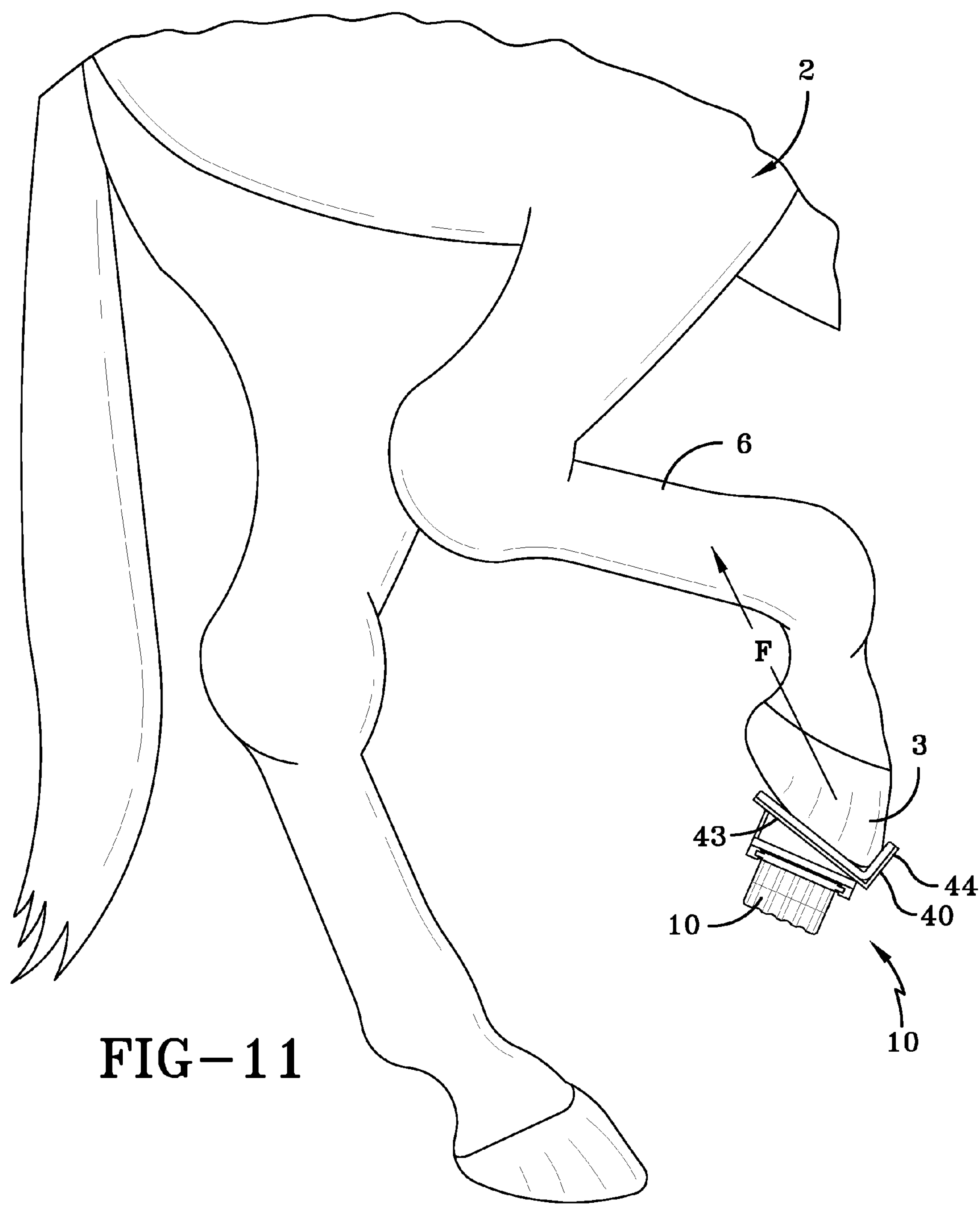

With reference to FIG. 11, the hoof holder assembly 40 is attached to the device 100 for evaluating the hind upper limb 6, in this case the hoof 3 is positioned such that the bottom of the hoof 3 is placed on the planar surface 43 with the "L" shaped bent up portion 44 used to prevent the hoof 3 from slipping off, in this case the entire limb 6 is then raised up towards the body of the horse 2 in such a fashion that the force is applied on the hoof 3 as the leg 6 is bent in an upward position.

Figure 12:
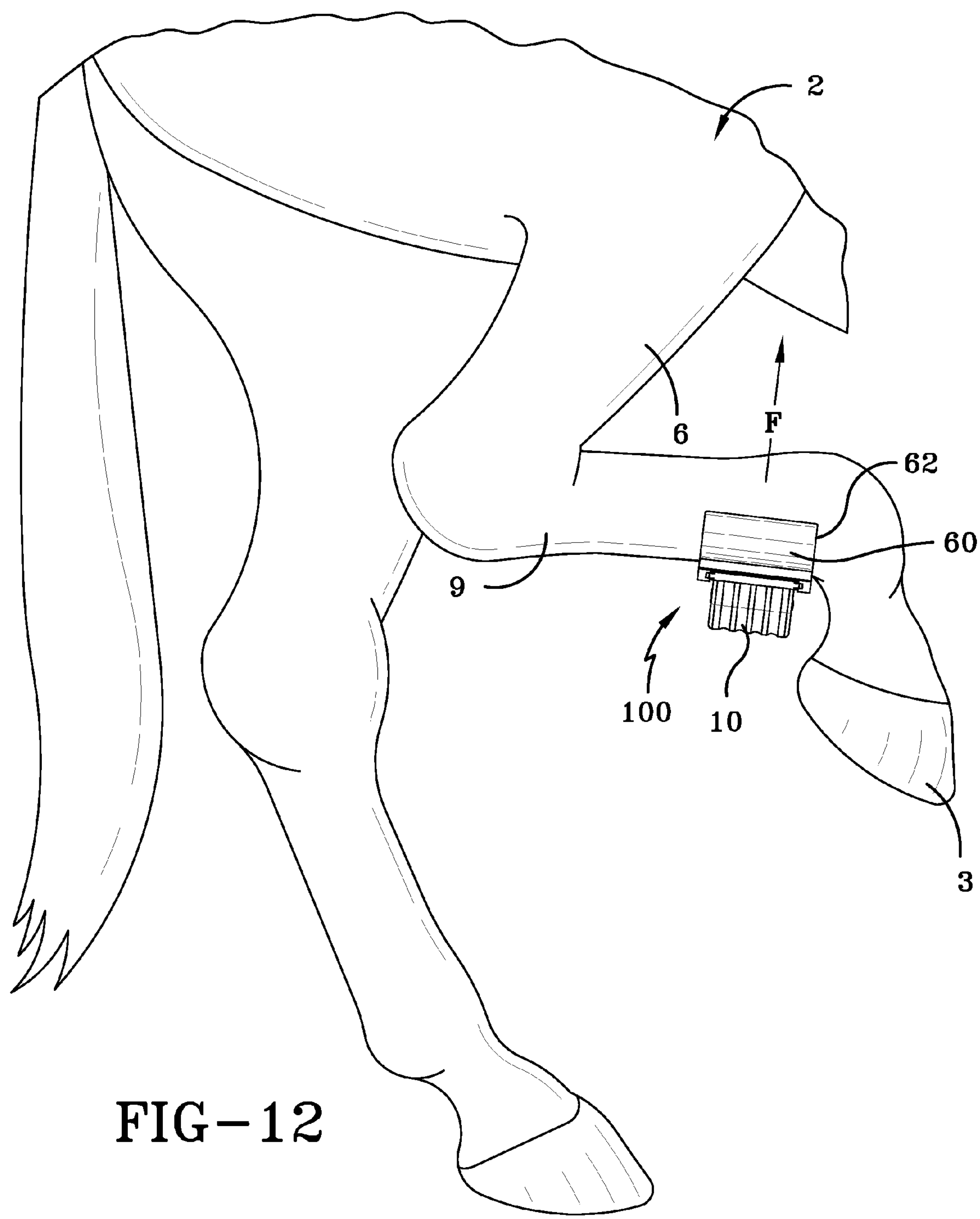

With reference to FIG. 12, the leg holder assembly 60 is applied to a hind upper limb 6 of a test animal 2. The leg holder assembly 60 is placed directly adjacent the bent portion 9 of the lower leg at the ankle joint and the leg 6 is bent in an upward position. The leg holder assembly 60 supports the lower portion 9 of the leg in the "U" shaped cradle 62 as illustrated. The force is then applied and preferably a test is conducted for approximately 30-90 seconds, more preferably an average of one minute. In each case the force being applied to the animal is preferably on average about 150 newtons. This force is found to be an optimal average force. In each of the test conditions it is imperative that both the duration and amount of force applied be relatively consistent. In order to achieve these objectives, the device 100 is provided with an audible signal device 26 such that the tester can hear if the force applied is deviating from the preset amount. For example the device 100 can be set such that the low forces triggers at 140 or 145 newtons and the high forces triggers at 155 or 160 newtons, in such a condition no sound will be heard if the device is being held at the proper 150 newtons plus or minus 5 or plus or minus 10 depending on the selection of the test parameters. A timer is employed such that when the tester initiates a load on the load cell 50 an electronic circuit board 21 activates a timer 28 which will then indicate that the test condition has been completed. This can be done either by an audible sound or simply by the operator applying a load onto the load cell 50 to initiate the timer 28. When a one minute period or whichever time the operator has chosen for the test is achieved and the duration is completed an audible sound will beep indicating that the test has been completed. In this way the operator can successfully and uniformly apply the test for each of the various conditions shown through FIGS. 8-12.

Figure 13A:
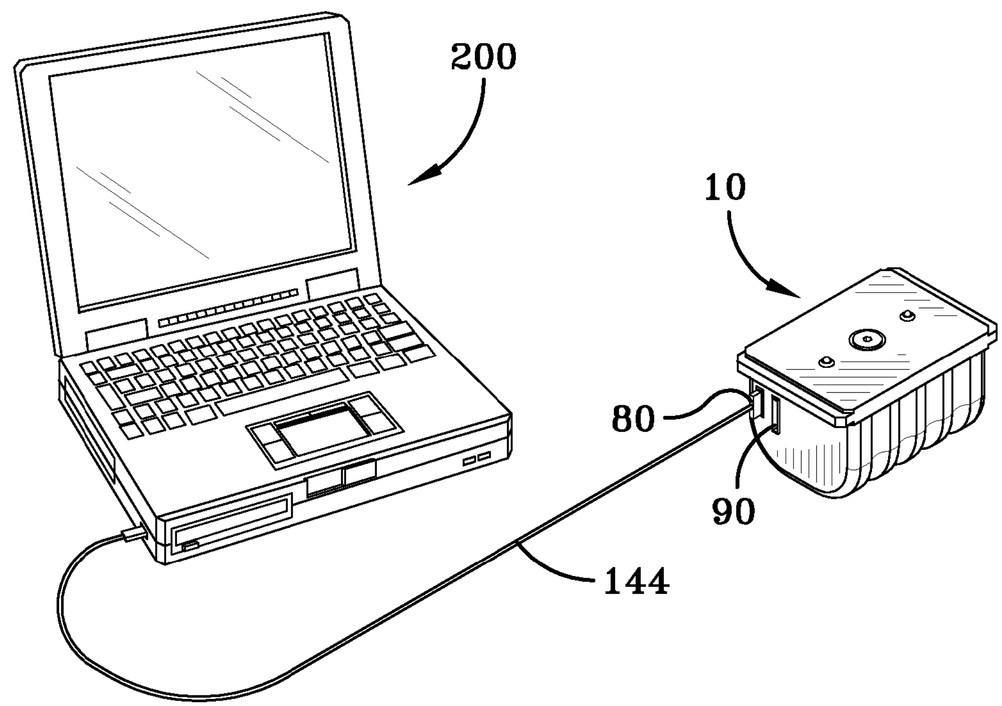
FIG. 13A-13D show various ways in which stored test data can be transferred to a data storage device such as a laptop computer or even a wireless receiver worn on a wrist of the tester.
Figure 13B:
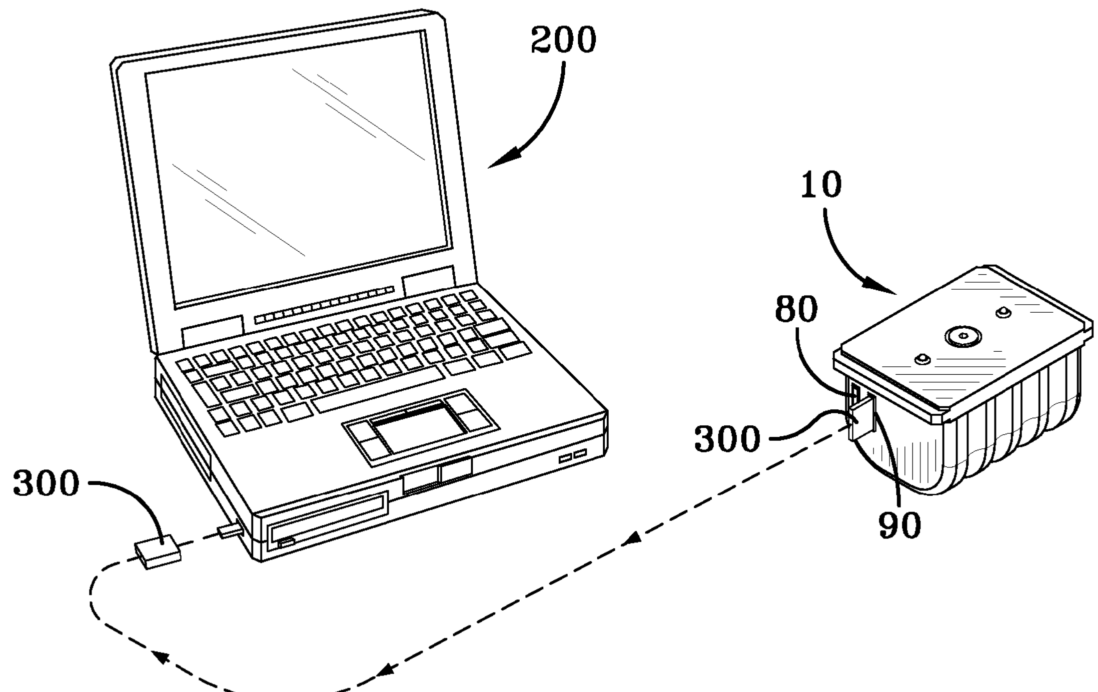
Figure 13C:
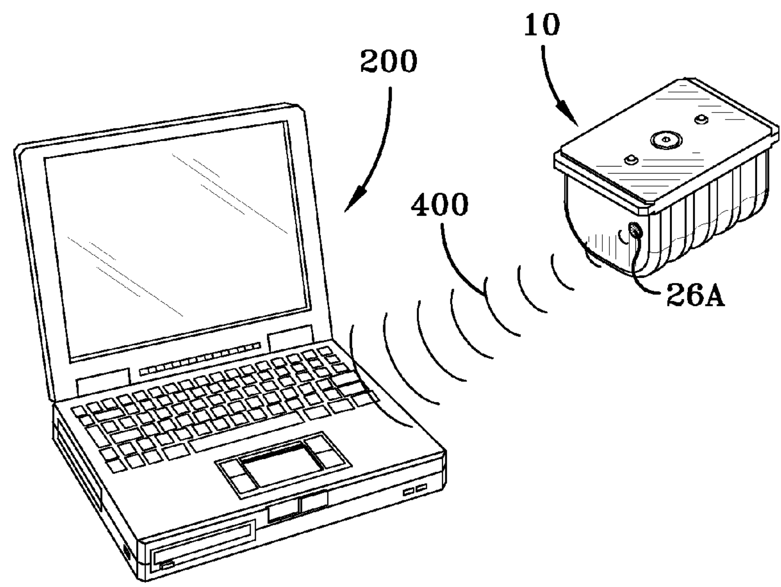

In FIGS. 13A-13D various ways in which stored data can be transmitted are shown. In FIG. 13A after testing is completed, the data can be transferred to a laptop computer 200 using a USB cable 144 connected to the module 10. In FIG. 13B this data transfer is shown as occurring by removing a flash card 300 from the module 10. In FIG. 13 the transfer occurs wirelessly using a wifi transmission 400.

Figure 13D:
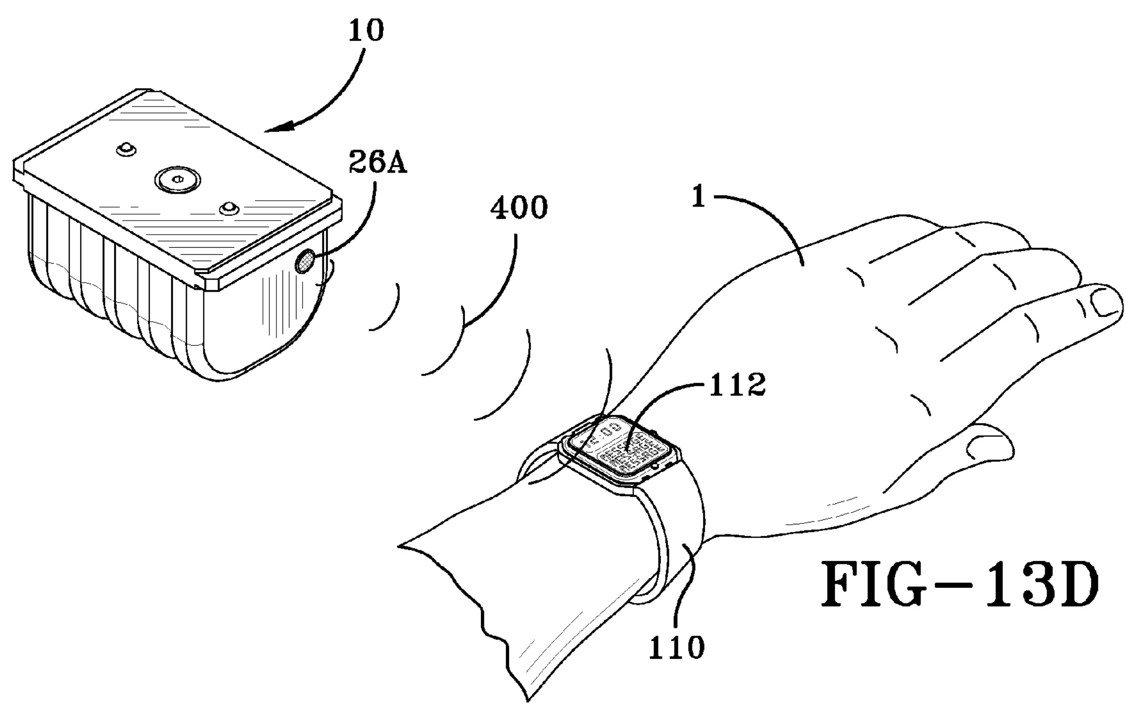

With reference to FIG. 13D, in this example the tester has a wrist attachment device 110 that communicates wirelessly with the handheld assembly module 10 in such a case this device 100 can provide a visual display 112 of the tester's load so that the tester can see precisely the load being applied if so desired. This optional feature can be provided with the present device and as such the operator 1 can maintain even more precise control over the assembly 100 as needed.

While the illustrated embodiments show that the deviations can be between 5 and 10 newtons plus or minus, it is also possible to set the device 100 more precisely such that audible sounds are heard anytime that the deviation is more than one Newton. In such a condition the evaluator will then hear sounds or alarms if he deviates from the desired optimal range.

As shown the device 100 can be set for any amount of accuracy needed or for any particular duration.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

The invention claimed is:

1. A cordless handheld equine leg flexibility testing device comprises:

a handheld assembly module having a housing and a load sensor cell attached to the housing, a base plate attached to the load sensor cell and spaced from the housing;

a leg holder assembly for removably attaching to the base plate of the handheld assembly, the leg holder assembly is shaped to support and apply force on the leg during testing;

a hoof holder assembly for removable attachment to the base plate of the handheld assembly, the hoof holder assembly being interchangeable with the leg holder assembly, the hoof holder assembly is shaped to support and immobilize the hoof and apply force during testing;

a power source for activating the load cell located in the housing;

a data storage module internal of the housing for receiving data from the load cell to collect force measurements exhibited by deflection of the load cell during testing and for transmitting the received data to a computer or a chart recording device after testing;

an audible sound device, the audible sound device signals the tester when the force applied deviates from a preset amount and when the duration of the test is achieved;

a timer activated when a load is applied to the load cell, the timer activates the audible sound device to beep when the test duration is achieved; and wherein flexion testing of the limb of a horse is achieved by bending the hoof under a constant force for a time duration between 30-90 seconds using the hoof holder assembly when attached to the device cradling the hoof and wherein the leg holder assembly when attached to the device holds the horses lower leg above the hoof under a constant force for between 30-90 seconds.

2. The cordless handheld equine leg flexibility testing device of claim 1 further comprises:

an electronic circuit board connected to the load circuit for measuring the start and duration of a test and the force being applied;

an audio signal device connected to the electronic circuit board to provide an audible tone indicating the completion of a test and any overloading or underloading forces by emitting audible sound alarms.

3. The cordless handheld equine leg flexibility testing device of claim 1 wherein the hoof holder assembly and the leg holder assembly have a conformable surface for contacting and supporting a test animal's leg or hoof.

4. The cordless handheld equine leg flexibility testing device of claim 3 wherein the conformable surface is an elastomeric material.

5. The cordless handheld equine leg flexibility testing device of claim 4 wherein the elastomeric material is a compressible polyurethane foam with an outer skin.

6. The cordless handheld equine leg flexibility testing device of claim 1 wherein the leg holder is arcuately curved transverse to the length of the leg holder to form a substantially parallel supporting surface for a limb of the test animal relative to the handheld assembly module.

7. The cordless handheld equine leg flexibility testing device of claim 1 wherein the hoof holder has an inclined "L" shaped surface relative to the handheld assembly module extending from an upper end to a lower end and along a length in a substantially planar surface; at the lower end a short bent portion extends from the planar surface to form the "L" shape for supporting and immobilizing the hoof of a test animal.

8. The cordless handheld equine leg flexibility testing device of claim 1 wherein the leg holder assembly and the hoof holder assembly each have mounting structures below the support surfaces, the mounting structures being for slidable attachment to the base plate of the handheld assembly module; and wherein the base plate has protruding guide surfaces for accepting the mounting structures, and the mounting structures have complimentary guide channels for sliding onto the protruding guide surfaces.

9. The cordless handheld equine leg flexibility testing device of claim 8 wherein the base plate and the mating mounting structures further comprise a detent locking pin and hold assembly for removable attachment.

10. The cordless handheld equine leg flexibility testing device of claim 2 wherein the handheld assembly further includes a wifi transmitter assembly connected to the circuit board for wireless transmission of data.

11. The cordless handheld equine leg flexibility testing device of claim 2 wherein the handheld assembly further has a port for a removable electronic flash card to be connected to the circuit board for data storage retrieval.

12. The cordless handheld equine leg flexibility testing device of claim 2 wherein the handheld assembly further has a USB port connected to the circuit board to permit stored data to be downloaded to a computer after testing.

13. The cordless handheld equine leg flexibility testing device of claim 12 further comprises a remote load indicator device for attachment to the wrist of the tester, the remote indicator device has a visual load display activated by a wireless transmission from the handheld assembly.

14. The cordless handheld equine leg flexibility testing device of claim 1 wherein the base plate has a centrally located attachment hemispherical locator post and each leg holder assembly and hoof holder assembly is removably attached to the hemispherical shape locator post wherein each holder assembly can pivotably move slightly relative to the handheld assembly module.

15. A cordless handheld equine leg flexibility testing device comprises:

a handheld assembly module having a housing and a load sensor cell attached to the housing, a base plate attached to the load sensor cell and spaced from the housing;

a leg holder assembly for removably attaching to the base plate of the handheld assembly, the leg holder assembly has a U shaped structure to support and apply force on the leg during testing;

a hoof holder assembly for removable attachment to the base plate of the handheld assembly, the hoof holder assembly being interchangeable with the leg holder assembly, the hoof holder assembly has an inclined L shaped structure for supporting and immobilizing the hoof and applying force during testing;

a power source for activating the load cell located in the housing;

a data storage module internal of the housing for receiving data from the load cell to collect force measurements exhibited by deflection of the load cell during testing and for transmitting the received data to a computer or a chart recording device after testing;

an audible sound device, the audible sound device signals the tester when the force applied deviates from a preset amount and when the duration of the test is achieved;

a timer activated when a load is applied to the load cell, the timer activates the audible sound device to beep when the test duration is achieved; and wherein flexion testing of the limb of a horse is achieved by bending the hoof under a constant force for a time duration between 30-90 seconds using the hoof holder assembly when attached to the device cradling the hoof and wherein the leg holder assembly when attached to the device holds the horses lower leg above the hoof under a constant force for between 30-90 seconds.

* * * * *